(12) United States Patent
Greenwald et al.

(10) Patent No.: US 7,837,640 B2
(45) Date of Patent: Nov. 23, 2010

(54) DYNAMIC BODY PROTECTOR

(75) Inventors: Richard M. Greenwald, Norwich, VT (US); Jeffrey J. Chu, Norwich, VT (US); Alexander W. Jessiman, Wilmington, DE (US); Aaron T. Buck, West Lebanon, NH (US); David W. Bertoni, Beverly Farms, MA (US); Joseph T. Gwin, White River Junction, VT (US)

(73) Assignee: Simbex LLC, Lebanon, NH (US)

( * ) Notice: Subject to any disclaimer, the term of this patent is extended or adjusted under 35 U.S.C. 154(b) by 0 days.

(21) Appl. No.: 11/780,115

(22) Filed: Jul. 19, 2007

(65) Prior Publication Data

US 2008/0146981 A1    Jun. 19, 2008

Related U.S. Application Data

(60) Provisional application No. 60/832,363, filed on Jul. 21, 2006.

(51) Int. Cl.
    *A61F 5/00*    (2006.01)
(52) U.S. Cl. .......................................... 602/20; 602/21
(58) Field of Classification Search ............... 602/5, 602/20–23; 2/18, 161.1; 446/267; 128/877–879
    See application file for complete search history.

(56) References Cited

U.S. PATENT DOCUMENTS 2,146,933 A * 2/1939 Budin ......................... 602/30
4,011,596 A   3/1977 Chang (Continued)

OTHER PUBLICATIONS

Centers for Disease Control and Prevention. Incidence and Costs to Medicare of Fractures Among Medicare Beneficiaries Aged greater than or equal to 65 years—United States, Jul. 1991-Jun. 1992. Morbidity and Mortality Weekly Report 1996; 45(41): 877-883.

(Continued)

*Primary Examiner*—Michael A. Brown
(74) *Attorney, Agent, or Firm*—Barlow, Josephs & Holmes

(57) ABSTRACT

The present invention provides a novel means of joint and body protection using engineered textiles to provide dynamic kinematic control within the device itself and for the underlying body part. The apparatus may be used in apparel or orthosis wherein a textile is organized about the proximal and distal aspects of a joint or body part and uses the mechanical and material characteristics of the engineered textile to dynamically control the kinetics of the body part and more specifically to prevent the body part from reaching extremes in range of motion. The engineered textiles can be designed to provide non-uniform increases in stiffness in any direction. The engineered textile may incorporate strain or strain rate dependant materials in which case stiffness properties would vary non-uniformly with velocity and/or acceleration within the device allowing for protection from blunt trauma, blast, or ballistic events anywhere on the body. A further aspect of the present invention is to provide a novel means of dynamically fitting and anchoring apparel, orthosis, body protection devices or other objects that need to be securely fixed to the body anatomy during joint flexion or extension, by using motion at a body joint to actuate a closure mechanism and bracing system that actively closes upon the body anatomy surrounding the joint and transfers loads created during dynamic restraint of the joint to anchor zones on the body.

12 Claims, 3 Drawing Sheets

U.S. PATENT DOCUMENTS

| | | | |
|---|---|---|---|
| 4,062,073 | A | 12/1977 | Rhee |
| 4,193,135 | A | 3/1980 | Rhee |
| 4,856,500 | A | 8/1989 | Spademan |
| 4,958,384 | A | 9/1990 | McCrane |
| 5,000,169 | A | 3/1991 | Swicegood et al. |
| 5,002,045 | A | 3/1991 | Spademan |
| 5,046,490 | A | 9/1991 | Young et al. |
| 5,150,475 | A | 9/1992 | Hansen et al. |
| 5,313,667 | A | 5/1994 | Levine |
| 5,339,465 | A | 8/1994 | Kyewski |
| 5,435,007 | A | 7/1995 | Kalvestran et al. |
| 5,451,203 | A * | 9/1995 | Lamb .................. 602/36 |
| 5,458,564 | A | 10/1995 | Franzen |
| 5,459,878 | A | 10/1995 | Gold |
| 5,526,531 | A | 6/1996 | Olson et al. |
| 5,566,389 | A | 10/1996 | Li |
| 5,600,849 | A | 2/1997 | Hu |
| 5,652,955 | A | 8/1997 | Skewis |
| 5,653,580 | A | 8/1997 | Cruz |
| 5,685,013 | A | 11/1997 | Hausman |
| 5,720,047 | A * | 2/1998 | Spitzer .................. 2/161.1 |
| 5,722,092 | A | 3/1998 | Borzecki et al. |
| 5,725,490 | A | 3/1998 | Conran |
| 5,778,449 | A | 7/1998 | Oetting et al. |
| 5,787,501 | A | 8/1998 | Coleman |
| 5,813,050 | A | 9/1998 | Popowski |
| 5,819,313 | A | 10/1998 | McCrane |
| 5,873,130 | A | 2/1999 | Lafferty |
| 5,898,936 | A | 5/1999 | Janes |
| 5,953,752 | A | 9/1999 | Jones |
| 5,983,408 | A * | 11/1999 | Li .................. 2/455 |
| 5,987,641 | A | 11/1999 | Walker |
| 6,014,770 | A * | 1/2000 | Spector .................. 2/18 |
| 6,024,715 | A | 2/2000 | Maxwell |
| 6,102,880 | A | 8/2000 | Nelson et al. |
| 6,913,802 | B1 | 7/2005 | Plant |
| 7,033,330 | B2 | 4/2006 | de Lint |

OTHER PUBLICATIONS

Malanga, G., Stuart, M., "In-Line Skating Safety Statistics", National Electronic Injury Surveillance System, 1995 Mayo Clinic Proceedings 70, 752-754.

Greenwald R.M., Senner V., Swanson S.C., "Biomechanics of Carving Skis", 2001 Sportmedizin und Sporttraumatologie, 49(1): 40-44.

Sasaki K., Takagi M., Kiyoshig Y., Ogino T., "Snowboarder's wrist: its severity compared with alpine skiing" 1999 The Journal of Trauma: Injury, Infection, and Critical Care 46, 1059-1061.

Idzikowski J., Janes P., Abbot P., "Upper extremity snowboarding injuries: ten-year results from the Colorado Snowboard Injury Survey" 2000 The Merican Journal of Sports Medicine 28, 825-832.

O'Neill D., McGlone M., "Injury risk in first-time snowboarders versus first-time skiers", 1999, The American Journal of Sports Medicine 27, 94-97.

National Institute of Arthritis and Musculoskeletal and Skin Diseases, "Osteoporosis: Progress and Promise", Health Topics, Aug. 2000.

US Consumer Product Safety Commission, "CPSC Projects Sharp Rise in In-Line Skating Injuries", News from CPSC, Jun. 21, 1995, Release #95-135.

Lewis L., West O., Standeven J., Jarvis H., "Do wrist guards protect against fractures", Annals of Emergency Medicine, Jun. 1997, 29, 766-769.

Staebler M., Moore D., Akelman E., Weiss A., Fadale P., Crisco J., "The effect of wrist guards on bone strain in the distal forearm", The American Journal of Sports Medicine, 1999, 27, 500-506.

Schieber R., Branche-Dorsey C., Ryan G., Rutherford G., Stevens J., O'Neill J., "Risk factors for injuris from in-line skating and the effectiveness of safety gear", The New England Journal of Medicine, 1996, 335, 1630-1635.

Orenstein J., "Injuries and small-wheel skates", Annals of Emergency Medicine, 1996, 27, 204-209.

Greenwald R.M., Janes P., Swanson S. C., MacDonald T. R., "Dynamic Impact Response of Human Cadaveric Forearms Using a Wrist Brace", American Journal of Sports Medicine, 1998, 26(6): 1-6.

* cited by examiner

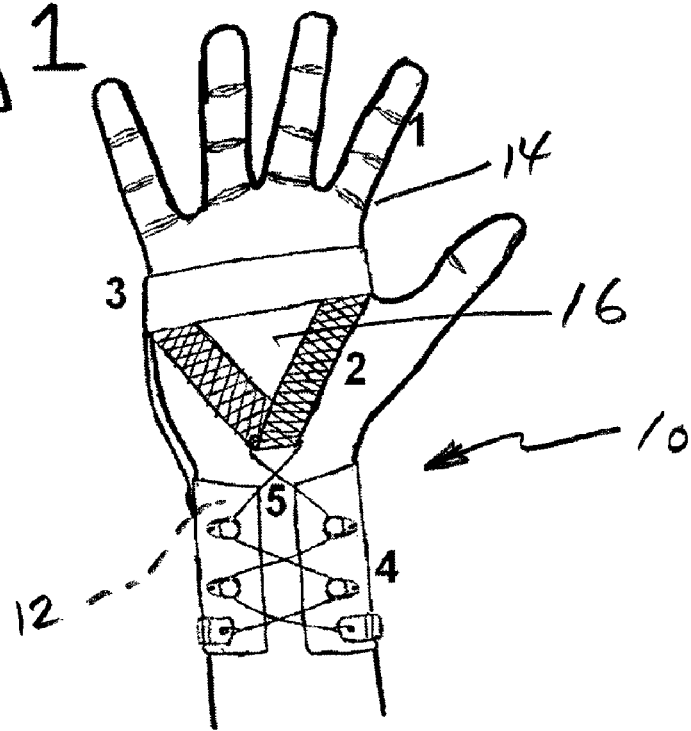
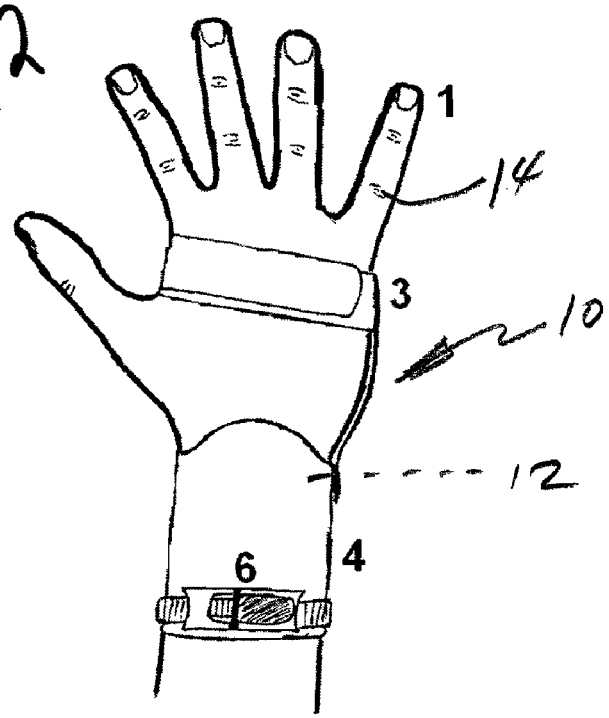

DYNAMIC BODY PROTECTOR

CROSS-REFERENCE TO RELATED APPLICATION

This application claims the benefit of the Provisional Application No. 60/832,363, filed Jul. 21, 2006, which is incorporated herein by reference.

STATEMENT REGARDING FEDERALLY SPONSORED RESEARCH OR DEVELOPMENT

The invention described herein was made in the course of work under grant number 2R44AR049959-02A1 from the National Institutes of Health. The U.S. Government may retain certain rights in this invention.

BACKGROUND OF THE INVENTION

The present invention relates to the field of protective equipment, specifically orthosis and/or apparel that serves as a body guard or body protector.

More particularly, it relates to a dynamic joint motion control system which is typically worn while participating in a sport or active recreational activity such as skiing or snowboarding. The present invention also relates to a system of dynamically fitting and anchoring body protection devices by using motion at a body joint to actuate a closure mechanism that actively closes upon the body anatomy surrounding the joint.

It should be understood that the present invention relates generally to kinematic control of body joints or body parts, and most importantly, to the prevention of terminal extension or flexion at a body joint. The present invention, as will be discussed in detail below, is capable of restraining the relative motion of any body part of an individual but has particular application in preventing terminal wrist dorsiflexion, also referred to as terminal wrist extension. Therefore, any reference to a body joint or body part is understood to encompass the wrist and any reference to the wrist alone is intended to include applicability to any body part. For ease of discussion and illustration, discussion of the prior art and the present invention is directed to the human wrist, by way of example and is not intended to limit the scope of discussion to the human wrist.

Excessive motion of body joints or excessive impact loads to the body can cause serious injury or death. There is a need to protect soldiers, athletes, industrial workers and economic animals from over-stressing parts of their anatomy when linear and/or rotational joint motion (displacement, velocity, acceleration) exceeds critical levels or when the body is struck by impact blows.

There are several joints that need this kind of protection including (but not limited to) the knee, ankle, wrist, thumb, fingers, shoulder, ankle, neck, and elbow. Excessive joint motion can result in fractures, sprains, and other problems. In order to prevent such injuries, it is desirable to dynamically control rotational and/or translational displacement and velocity of a body part.

For example, in sports such as snowboarding and in-line skating as well as in the elderly population, wrist injuries are common. The Centers for Disease Control and Prevention (CDC) have reported significant wrist fracture data in 3 segments of the population: in-line skaters, snowboarders, and the elderly, particularly osteoporotic women (Table 1). See Centers for Disease Control and Prevention. Incidence and Costs to Medicare of Fractures Among Medicare Beneficiaries Aged greater than or equal to 65 Years—United States, July 1991-June 1992. Morbidity and Mortality Weekly Report. 1996; 45(41): 877-883.

The 1996 National Electronic Injury Surveillance System (NEISS) data for in-line skating estimates almost 300,000 injuries per year, of which as high as 56% have been reported as wrist injuries. See National Electronic Injury Surveillance System, *In-Line Skating Safety Statistics*, 1996, accessed at http://www.iisa.org/resources/safety.htm#1996%20injuries on Jun. 27, 2002 and Malanga, G., Stuart, M., 1995. *In-line skating injuries*. Mayo Clinic Proceedings 70, 752-754.

The incidence of wrist fracture in snowboarding has been reported as high as 1.02 fractures per 1000 snowboarder days. Greenwald R M, Senner V, Swanson S C: *Biomechanics of Carving Skis*, Sportmedizin und Sporttraumatologie, 49(1): 40-44, 2001. Wrist injuries as a percentage of total snowboarding injuries have been reported between 18.7% and 21.6%. Sasaki, K., Takagi, M., Kiyoshige, Y., Ogino, T., 1999. *Snowboarder's wrist: its severity compared with alpine skiing*. The Journal of Trauma: Injury, Infection, and Critical Care 46, 1059-1061 and Idzikowski, J., Janes, P., Abbot, P., 2000. *Upper extremity snowboarding injuries: ten-year results from the Colorado Snowboard Injury Survey*. The American Journal of Sports Medicine 28, 825-832.

Of first-time snowboarders, 53% of injuries are upper extremity injuries. See O'Neill, D., McGlone, M., 1999. *Injury risk in first-time snowboarders versus first-time skiers*. The American Journal of Sports Medicine 27, 94-97. The CDC reports that wrist fracture is the second most-common fracture among the elderly, with an incidence of 37.8 per 10,000 population. This cost to Medicare is projected at $226 million per year in 1996 dollars. Additionally, NIH reports that over 250,000 wrist fractures annually are caused by osteoporosis. See National Institute of Arthritis and Musculoskeletal and Skin Diseases, *Osteoporosis: Progress and Promise*. Health Topics, August 2000, accessed at http://www.niams.nih.gov/hi/topics/osteoporosis/opbkgr.htm on Jun. 27, 2002.

TABLE 1

Incidence and cost of wrist fractures in the United States

| Wrist Fx | Incidence/year (000's) | Incidence/1000 exposures | Associated Medical Costs ($M's) |
|---|---|---|---|
| In-line skating | 168 | 0.27 | $18 |
| Snowboarding | 34 | 1.02 | $4 |
| Falls in the elderly | 250 | 0.38 | $226 |

See also US Consumer Product Safety Commission, *CPSC Projects Sharp Rise in In-Line Skating Injuries*, NEWS from CPSC, accessed at http://www.cpsc.gov/CPSCPUB/PREREL/PRHTML95/95135.html on Jul. 22, 2002. If the wrist is prevented from reaching terminal extension, it is possible to prevent fracture of the wrist bones. In prior art, conventional wrist guards are typically constructed from fabric with rigid aluminum or rigid plastic plates or splints crossing the wrist joint on either the dorsal or volar surface of the hand as a protection mechanism against abrasions and/or carpal fractures, including the wrist. Prior art guards limit normal range of motion at the wrist as well as increasing the torque required to achieve terminal wrist extension during an impact event. Biomechanical studies of wrist guard efficacy using matched pairs of cadavers showed that wrist guards increased the force to wrist fracture and absorbed a small percentage of the impact energy following a dynamic impact. See Lewis, L., West, O., Standeven, J., Jarvis, H., 1997. *Do wrist guards protect against fractures?* Annals of Emergency Medicine 29, 766-769.

Wrist guards were also shown to act in a load-sharing capability by reducing bone strain in the dorsal distal radius during both quasi-static and dynamic loading. See Moore, D. C., Staebler, M. P., Crisco, J. J., Greenwald, R. M., Akelman, E., Weiss, A 2000. *Wrist guards reduce impact-generated bone strain in the distal radius.* In Transactions of the 46th meeting of the Orthopaedic Research Society. Orthopaedic Research Society, Rosemont and Staebler, M., Moore, D., Akelman, E., Weiss, A., Fadale, P., Crisco, J., 1999. *The effect of wrist guards on bone strain in the distal forearm.* The American Journal of Sports Medicine 27, 500-506. Wrist guards also offer the possibility of reducing the friction between the hand and the impact surface. This is particularly important in in-line skating, where the impact surface is often concrete. Clinically, wrist guards limit the incidence and severity of wrist injury. See Schieber, R., Branche-Dorsey, C., Ryan, G., Rutherford, G., Stevens, J., O'Neill, J., 1996. *Risk factors for injuries from in-line skating and the effectiveness of safety gear.* The New England Journal of Medicine 335, 1630-1635 and Orenstein, J., 1996. Injuries and small-wheel skates. Annals of Emergency Medicine 27, 204-209.

While, force to fracture increased by approximately 50% with wrist guard use, conventional wrist guards did not prevent terminal wrist extension. For relatively high energy impacts, there was no decrease in loading rate near terminal extension with or without a wrist guard, indicating that the effectiveness of the wrist guard is overwhelmed at higher loading rates. See Greenwald R M, Janes P S, Swanson S C, MacDonald T R: *Dynamic Impact Response of Human Cadaver Forearms Using a Wrist Brace*, American Journal of Sports Medicine. 26(6):1-6, 1998.

Commercially available wrist guards reduce wrist injury incidence and severity, but they suffer from a lack of use in the population most at risk for wrist injuries. Only 2-7% of snowboarders used wrist splints over a eight year study period. See ldzikowski, J., Janes, P., Abbot, P., 2000. *Upper extremity snowboarding injuries: ten-year results from the Colorado Snowboard Injury Survey.* The American Journal of Sports Medicine 28, 825-832. The primary reason appears to be that the available guards restrict normal range of motion, and are too bulky for most users. In general, epidemiological and biomechanical studies support the conclusion that the use of wrist protection for in-line skating and snowboarding significantly reduces the incidence and severity of wrist fractures. The problem is that very few people actually wear the protective devices because they limit normal range of motion and are generally bulky and unappealing.

In view of the foregoing, there is a demand for a joint motion control system which is low profile, light weight, non-bulky, and non-restrictive to normal range of motion, yet still prevents terminal wrist extension and increases the force to fracture.

The present invention is provided to solve the problems discussed above and other problems, and to provide advantages and aspects not provided by prior designs of this type. A full discussion of the features and advantages of the present invention is deferred to the following detailed description, which proceeds with reference to the accompanying drawings.

SUMMARY OF THE INVENTION

The present invention is generally directed to a novel and unique means of providing body and joint protection using engineered textiles to dynamically control the kinematics within the device itself and of the underlying body part. The apparatus enables free range of motion until a predefined level of linear and/or rotational joint motion (position, velocity, or acceleration) is achieved, at which point the engineered textile is engaged to provide linear or non-linear progressive restraint of motion at a body joint.

While the present invention is specifically developed for the wrist, and while the present invention is designed to engage based on wrist joint position, motion control of other body joints and motion control based on body joint velocity and/or acceleration is envisioned and considered within the scope of the present invention.

The present invention enables the prevention of terminal wrist extension and increases the force required to cause wrist fracture without limiting normal range of motion. Specifically, wrist flexion is uninhibited and wrist extension is uninhibited until the wrist extension angle exceeds a pre-determined threshold at which point the guard engages to dampen wrist motion and resist terminal extension. In the present invention engineered textiles are organized about the distal and proximal aspects of the joint and utilize the mechanical and material characteristics of the engineered textile to dynamically control the motion of the joint. However, hydraulic, electro-mechanical, mechanical, and other means are also envisioned for dynamically controlling joint displacement.

The present invention was designed as a stand-alone dynamic body protection device. However, the system and method of the present invention are designed such that the apparatus can be integrated into apparel, conventional braces, or any other medium surrounding the body joint.

Another aspect of the present invention is to provide velocity or acceleration dependant dynamic control of the kinematics of a body part or other object by using non-linear (strain dependant and/or strain rate dependant) materials. Engineered textiles integrated with strain-rate dependent materials afford stiffness and damping properties which can be tuned to dynamically control the kinematics of a body part or other object based on the requirements of the protective equipment. In the present embodiment, strain rate dependant materials are encapsulated within the textile, which is organized about the proximal and distal endpoints of the joint, to provide velocity dependant energy damping.

A further aspect of the present invention is to provide a novel means of dynamically fitting and anchoring apparel, orthosis, braces, body protection devices, or other objects that need to be securely fixed to the body anatomy during joint flexion or extension, by using motion at a body joint to actuate a closure mechanism and bracing system that actively closes upon the body anatomy surrounding the joint and transfers loads created during dynamic restraint of the joint to anchor zones on the body. The present invention uses relative motion between two sides of the body joint to activate a closure system, such as lacing, straps, or other mechanical or electro-mechanical means, that dynamically and progressively tightens or loosens the device around the body in response to joint motion.

Other features and advantages of the invention will be apparent from the following specification taken in conjunction with the following drawings.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

FIG. 1 is a volar view of the preferred embodiment on an individual's wrist;

FIG. 2 is a dorsal view of the preferred embodiment shown in FIG. 1;

DETAILED DESCRIPTION OF THE PREFERRED EMBODIMENT

Figure 3:
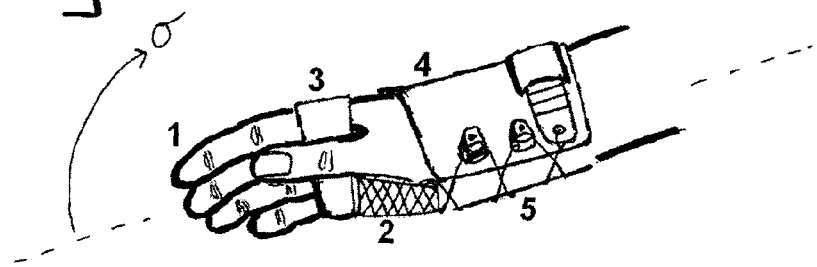
FIG. 3 is a perspective view of the preferred embodiment shown in FIG. 1.

This invention is applicable to many embodiments and to motion control of many objects or body parts. Shown in the drawings and herein described in detail is a preferred embodiment of the invention with the understanding that the present disclosure is to be considered as an exemplification of the invention and is not intended to limit the scope of the invention to the embodiment described and illustrated.

The present invention provides a system 10 for dynamically controlling body joint position and velocity without limiting normal range of motion at the body joint. The body joint 12 will be described below as the wrist joint 12, but the scope of the invention is not limited only to the wrist. Unlike the prior art, the current invention allows for normal range of motion and only engages after a predefined wrist extension angle is achieved. Additionally, unlike the prior art the current invention is dynamically anchored to the body anatomy. In other words, the guard becomes tighter during an impact event and looser for comfort otherwise.

FIG. 1 shows a volar view of the system 10 of the current invention on a human hand 1. Motion at the wrist joint 12 is controlled by an engineered textile palm strap 2 which is directly attached to an tenacious and stiff overhand strap 3 which goes around the hand 1 just proximal of the knuckles 14 and to a wrist cuff 4. During impact to the palm 16, as often occurs when falling, wrist extension, as defined by a positive angle Θ in FIG. 3, occurs and tensions the textile palm strap 2. The guard 10 begins to absorb impact energy at a predetermined wrist extension angle and is tuned so that the palm strap 2 textile is fully extended before terminal wrist extension. The preferred method of tuning the lockup angle is by adjusting the pre-tension in the palm strap 2, that is the tension that exists in the palm strap 2 during the nominal (pre-impact) state. The textile palm strap 2 is directly linked to the cuff lacing system 5 which consists of a high tenacity, low stretch, synthetic lace such as nylon and to the over arm buckle 6 which may be a ratchet buckle such as M2 International RB7-L. The pretension in the lacing system 5 and in the palm strap 2 is controlled by the over arm ratchet buckle 6. FIG. 2 shows a dorsal view of the present invention 10 on a human hand 1. The overhand strap 3 transfers force from the engineered textile palm strap 2 to the dorsal side of the hand 1. This is an adjustable strap 2 and may be Velcro or any other material suitable for this purpose.

Figure 4:
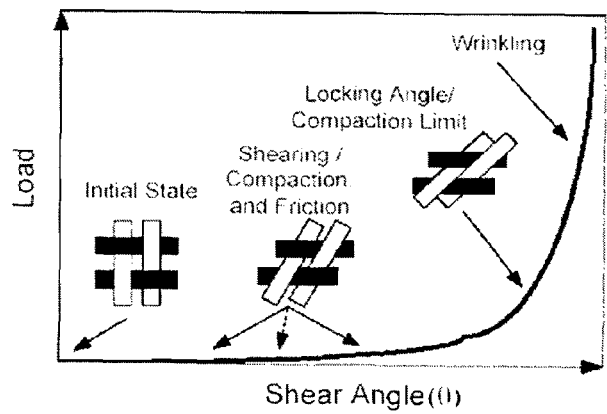
FIG. 4 is a graph showing the non-linear relationship of the angle between the fibers within the braided engineered textile also called the shear angle to the axial tension in the braided textile.
Figure 5A:
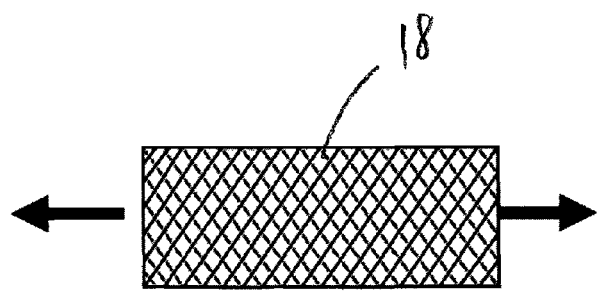
FIG. 5a is a front view of a braided textile under no load.
Figure 5B:
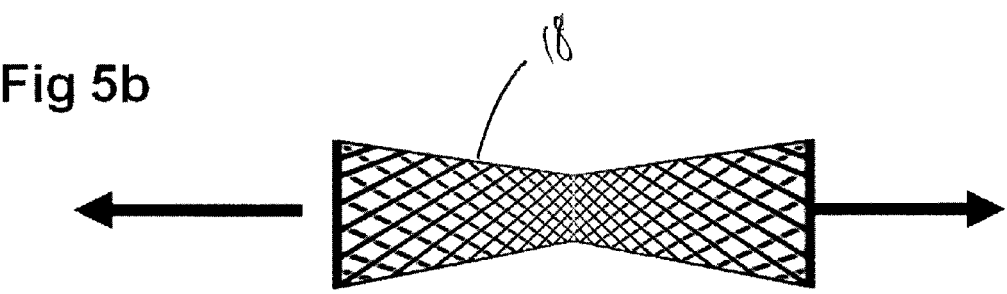
FIG. 5b is a front view of a braided textile under load.

In the present invention, the method of dynamically controlling wrist motion is carried out by an engineered textile which is seen in FIGS. 5a and 5b. The characteristics of this engineered material 18 is shown in the graph of FIG. 4, which will be discussed in further detail below. These engineered textiles 18 are organized about the distal and proximal aspects of the wrist joint and utilize the mechanical and material characteristics of the engineered textile 18 to dynamically control the motion of the joint and more specifically to prevent reaching extremes in range of motion of the joint. In joint orientations below a pre-determined threshold (for example Θ<45 degrees), the constituent fibers of the engineered textile 18 have minimal interaction and therefore slide freely relative to one another, as in FIG. 5a, allowing normal, relatively unrestricted joint motion. As the joint, such as wrist 12 shown in FIGS. 1 and 2, is moved beyond a positional threshold, in any direction, geometric changes such as fiber interaction within the textile 18 provide increasing stiffness, restraining and controlling further motion of the joint FIG. 5b. The engineered textile 18 can be designed to provide a non-uniform increase in stiffness in any direction. Specifically, the stiffness in one direction of movement may be different than the stiffness in another direction. The preferred material for the engineered textile is braided composite of aramid fiber (Technora, Teijin-Limited) and polyester, however, many combinations of engineered polymer or ceramic textiles are suitable and considered within the scope of the present invention. In the present invention, the engineered textile 18 to serve as palm strap 2 is covered in UV resistant material to increase durability.

Another aspect of the present invention is velocity dependant energy damping. The palm strap 2 can be encapsulated in or otherwise integrated with strain or strain-rate dependent materials. In the present invention, the engineered textile 18 is incorporated with a non-linear damping material to afford improved energy absorption and to improve the ability of the device to prevent terminal wrist extension. In another embodiment, the engineered textile 18 is incorporated with a non-linear strain-rate dependant material that could be used to control high impact velocity kinematics. Under high impact velocities, such as ballistic events, the strain rate dependent material exhibits dilatant non-Newtonian behavior such that material stiffness increases with strain rate creating an opposing force to control motion and/or deformation.

A further aspect of the present invention is a dynamic closure mechanism. The dynamic closure mechanism may be used to attach any object, the wrist cuff 4 and engineered textile 18 in the present invention, to the body surrounding a joint, such as wrist 12. Motion at the joint 12 is used to activate a closure mechanism which dynamically and progressively tightens or loosens upon the body in response to motion at the joint. In the present invention, tension in the engineered textile palm strap 2 in response to wrist extension activates the lacing system 5 which circumferentially tightens the wrist cuff 4. Additionally, the lacing system is directly attached to the over arm buckle 6. During wrist extension forces in the guard that are not absorbed by the engineered textile palm strap 2 are transferred to anchor zones on the body. In the present invention, those anchor zones are the dorsal forearm, the ulnar condyle, the radial condyle, the thumb webbing, and the dorsal side of the hand just proximal of the knuckles. The dynamic closure mechanism relieves the pressure on these five anchor points when the wrist extension angle is less than the predetermined threshold. When the predetermined threshold is exceeded, the tension in the engineered textile palm strap 2 activates the cuff closure and engages the five anchor zones. The benefit of this dynamic closure mechanism is increased comfort during normal use and dynamic tightening during impact to provide wrist protection.

EXPERIMENTAL TESTING

Laboratory testing demonstrated that the present invention offered less resistance to wrist motion for wrist angels (flexion or extension) less than the predefined lockup angle and engaged when wrist extension exceeded this angle, stopping wrist joint rotation at a lower peak extension angle and with a lower peak torque on the wrist joint than conventional wrist guards.

A twin rail linear drop system was used to drop a surrogate arm with a revolute wrist joint onto a 6 degree of freedom force plate such as Advanced Mechanical Technology Inc. MC6. The surrogate arm was positioned so that the surrogate forearm was parallel to the drop rails with the distal end pointing downward and the starting wrist joint angle was set at 30 degrees to prevent the fingers from stubbing on the force plate. The surrogate arm was instrumented with a draw wire potentiometer such as Micro Epsilon WPS-MK30 to measure wrist angle. The combined mass of the surrogate arm and the drop bar to which the surrogate arm was attached was 16 kg. The force plate was positioned at 10 degrees with respect to the horizontal floor plane so that the surrogate arm could revolve through 100 degrees during impact.

Four conventional wrist guards and the present invention were successively fit to the surrogate arm and dropped from 0.2 m, 0.3 m, and 0.6 m as measured from the force plate to the revolute wrist joint. Data were sampled at 10 K Hz and stored for processing. Inverse dynamics were used to transform forces and moments measured at the force plate to torques applied at the wrist joint. The present invention reduced peak wrist extension angles by as much as 20% compared to conventional wrist guards.

Additionally, static load testing was performed to quantify the resistance to wrist motion provided by each guard for normal range of motion, less than 45 degrees flexion or extension. A digital force gauge such as Checkline BG-10, was used measure the applied force at the finger webbing required to achieve wrist flexion and extension angles less than 45 degrees. The protection device 10 of the present invention offered less as much as 50% less resistance to wrist motion within the normal range of 45 degrees flexion or extension and engaged after the predetermined wrist extension threshold to protect from terminal extension.

It would be appreciated by those skilled in the art that various changes and modifications can be made to the illustrated embodiments without departing from the spirit of the present invention. All such modifications and changes are intended to be covered by the appended claims.

We claim:

1. A joint and body protection device for a protected body joint disposed between a first and second body part, comprising:
    an engineered textile, having a first end and a second end; the engineered textile including an plurality of overlapping fibers; the overlapping fibers being freely slidable relative to and in communication with each other to provide varying degrees of friction against each other and varying degrees of compaction of the fibers in response to an applied load; stiffness of the engineered textile thereby non-linearly increasing in response to the applied load;
    the first end being securable to the first body part and the second end being securable to the second body part with the engineered textile spanning across a protected body joint; the first end being securable to the first body part by a first means for anchoring and the second end being securable to the second body part by a second means for anchoring;
    a strain rate dependent damping material; the engineered textile being in communication with the strain rate dependant damping material so that stiffness in the engineered textile is a non-linear function of displacement, velocity, or acceleration;
    the engineered textile being configured to provide dynamic kinematic control of the protected body joint;
    wherein force between the first means for anchoring and the second means for anchoring is dynamically and progressively changed in response to motion of the protected joint so that the device can be loosened and progressively tightened as needed for protection of the protected joint.

2. The joint and body protection device of claim 1 wherein the engineered textile is tensioned and relaxed in response to movement at the protected body joint.

3. The joint and body protection device of claim 1 wherein the engineered textile is a braided fiber.

4. The joint and body protection device of claim 1 wherein the engineered textile is a high tenacity non-braided synthetic fiber.

5. The joint and body protection device of claim 1 wherein the engineered textile is removably connected to the strain rate damping material.

6. The joint and body protection device of claim 1 wherein the engineered textile is engaged to prevent terminal wrist dorsiflexion.

7. The joint and body protection device of claim 1 wherein the engineered textile is organized within a palm of a human hand; the first end of the engineered material being connected to the first means for anchoring that is securable to the forearm as well as the second end of the engineered material being connected to the second means for anchoring that is securable to the dorsal side of the hand.

8. The joint and body protection device of claim 7 wherein the engineered textile is connected to a lacing system such that the first means for anchoring tightens and loosens circumferentially in response to tension in the engineered textile caused by wrist dorsiflexion.

9. The joint and body protection device of claim 8 wherein the lacing system is indirectly connected about the dorsal forearm so that tension in the engineered textile as well as in the lacing system is transferred to pressure on the dorsal forearm.

10. The joint and body protection device of claim 8 wherein the lacing system is directly connected about the dorsal forearm so that tension in the engineered textile as well as in the lacing system is transferred to pressure on the dorsal forearm.

11. The joint and body protection device of claim 1 wherein the engineered textile is connected directly about the dorsal forearm such that tension in the engineered textile is transferred to pressure on the dorsal forearm.

12. The joint and body protection device of claim 1 wherein the engineered textile is connected indirectly about the dorsal forearm such that tension in the engineered textile is transferred to pressure on the dorsal forearm.

* * * * *